(12) United States Patent
Schafersman et al.

(10) Patent No.: US 7,815,608 B2
(45) Date of Patent: Oct. 19, 2010

(54) HIGH FLEX INTRODUCER ASSEMBLY

(75) Inventors: Jessica A. Schafersman, Drexel, MO (US); David E. Hartley, Wannanup (AU); David P. Biggs, Bloomington, IN (US)

(73) Assignees: William Cook Australia Pty. Ltd., Brisbane, Queensland (AU); Cook Incorporated, Bloomington, IN (US)

( * ) Notice: Subject to any disclaimer, the term of this patent is extended or adjusted under 35 U.S.C. 154(b) by 103 days.

(21) Appl. No.: 12/054,907

(22) Filed: Mar. 25, 2008

(65) Prior Publication Data

US 2008/0243222 A1 Oct. 2, 2008

Related U.S. Application Data

(60) Provisional application No. 60/921,351, filed on Apr. 2, 2007.

(51) Int. Cl.
*A61M 5/178* (2006.01)
(52) U.S. Cl. .................................. 604/164.01
(58) Field of Classification Search ............. 604/164.01
See application file for complete search history.

(56) References Cited

U.S. PATENT DOCUMENTS

| | | | |
|---|---|---|---|
| 3,539,034 A | 11/1970 | Tafeen | 128/221 |
| 4,239,042 A | 12/1980 | Asai | 128/218 |
| 5,190,528 A | 3/1993 | Fonger et al. | 604/171 |
| 5,205,830 A | 4/1993 | Dassa et al. | 604/164 |
| 5,300,032 A | 4/1994 | Hibbs et al. | 604/164 |
| 5,380,304 A | 1/1995 | Parker | 604/282 |
| 5,695,483 A * | 12/1997 | Samson | 604/526 |
| 5,891,112 A * | 4/1999 | Samson | 604/524 |
| 6,183,443 B1 | 2/2001 | Kratoska et al. | 604/164.03 |
| 6,638,268 B2 | 10/2003 | Niazi | 604/528 |
| 6,824,533 B2 * | 11/2004 | Risk et al. | 604/319 |
| 6,824,553 B1 * | 11/2004 | Samson et al. | 606/192 |
| 7,192,433 B2 * | 3/2007 | Osypka et al. | 606/108 |
| 2001/0034514 A1 | 10/2001 | Parker | 604/525 |
| 2003/0114831 A1 | 6/2003 | Wang et al. | 604/525 |
| 2003/0125712 A1 | 7/2003 | Zhou | 604/530 |
| 2004/0049157 A1 | 3/2004 | Plishka et al. | 604/164.09 |
| 2006/0200079 A1 | 9/2006 | Magnusson | 604/164.1 |

* cited by examiner

*Primary Examiner*—Nicholas D Lucchesi
*Assistant Examiner*—Diva Ranade
(74) *Attorney, Agent, or Firm*—Brinks Hofer Gilson & Lione

(57) ABSTRACT

An introducer assembly for accessing a target site in the anatomy of a patient includes a sheath having a proximal end and a distal end, and having a lumen extending therethrough. At least a portion of the sheath distal end has a curved configuration. A tapered dilator has a proximal end and a distal end, and is sized to be received in the sheath lumen. The dilator has a length such that at least a distal tip portion of the dilator extends beyond the distal end of the sheath when the dilator is received in the sheath lumen. The dilator may be formed of polyurethane, and has a stiffness not exceeding a stiffness of the sheath curved portion such that the sheath substantially maintains the curved configuration when the dilator is received in the sheath lumen.

20 Claims, 2 Drawing Sheets

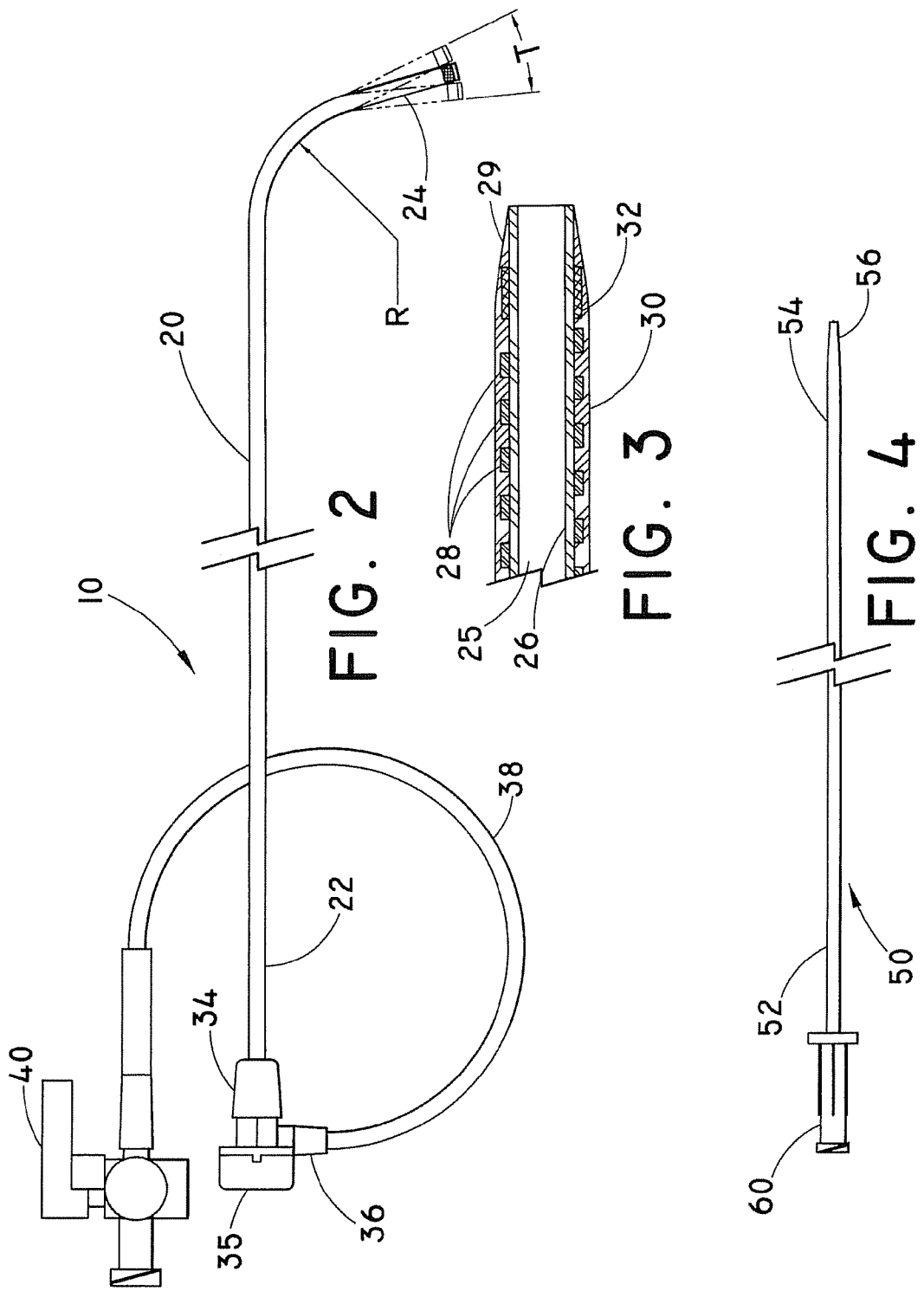

HIGH FLEX INTRODUCER ASSEMBLY

RELATED APPLICATION

The present patent document claims the benefit of the filing date under 35 U.S.C. §119(e) of Provisional U.S. Patent Application Ser. No. 60/921,351, filed Apr. 2, 2007, which is hereby incorporated by reference.

BACKGROUND

1. Technical Field

The present invention relates to an introducer assembly. More particularly, the present invention relates to an introducer sheath and dilator assembly having distal regions of high flexibility for use in accessing a target site in a tortuous portion of the patient's anatomy.

2. Background Information

A variety of well-known medical procedures are carried out by introducing an access device, such as a sheath, into a vessel in a patient's body. Typical procedures for introducing the device include the well-known Seldinger percutaneous entry technique. In the Seldinger technique, a needle is initially injected into the vessel, and a wire guide is inserted into the vessel through a bore of the needle. The needle is withdrawn, and an introducer assembly is inserted over the wire guide into the opening in the vessel. The introducer assembly typically includes an outer introducer sheath and an inner dilator having a tapered distal end. The tapered end of the dilator stretches the opening in the vessel in controlled fashion, so that introduction of the larger diameter introducer sheath may then be carried out with a minimum of trauma to the patient. Following satisfactory placement of the introducer sheath, the dilator is removed, leaving the larger diameter introducer sheath in place in the vessel. An interventional device, such as a catheter, stent, etc., may then be inserted through the introducer sheath into the vessel for placement at a target site within the vasculature.

Historically, these techniques have been problematic, due in large part to the lack of flexibility and/or kink resistance of the sheath. Early sheaths were typically formed of a relatively stiff fluorocarbon, such as polytetrafluoroethylene (PTFE) or fluorinated ethylene propylene (FEP). The sheaths were typically of thin-walled construction, and were prone to kinking, particularly when threaded through tortuous pathways within the body. Increasing the thickness of the sheath only minimally improved the kink resistance of the sheath. At the same time, the added thickness occupied valuable space in the vessel, thereby minimizing the diameter of the interventional device that could be passed therethrough. In addition, increasing the thickness of the sheath necessitated the use of a larger entry opening than would otherwise be required.

A kinked sheath is essentially unusable, and cannot be straightened while positioned in the body of the patient. Consequently, once a sheath kinks, the sheath must be removed, leaving an enlarged, bleeding opening which typically cannot be reused. Access to the vessel must then be re-initiated at an alternative site, and the process repeated with a new sheath. In many cases, a suitable alternative site is not available, and the percutaneous procedure must be abandoned altogether in favor of a different, and often more intrusive, technique.

In recent years, introducer sheaths have been improved in order to enhance their flexibility and kink resistance. Such sheaths are now routinely used to percutaneously access sites in the patient's anatomy that could not be accessed with prior art sheaths. Many such sheaths are also kink resistant through a high degree of bending. One example of a flexible, kink resistant introducer sheath is described in U.S. Pat. No. 5,380,304. The sheath described in this patent includes a lubricious inner liner having a helical coil fitted over the liner. An outer tube is connected to the outer surface of the liner through the coil turns. The sheath described in this patent is thin-walled, and, due to the presence of the coil reinforcement, is kink resistant through a wide range of bending.

U.S. Patent Publication 2001/0034514 discloses an introducer sheath similar in many respects to the sheath of the '304 patent. However, the sheath in the patent publication is formed such that the proximal end of the sheath has a higher stiffness, while the distal end has a lower stiffness. Since the distal portion of the sheath has a lower stiffness (and therefore is more flexible) than the proximal portion, the sheath is able to traverse portions of the anatomy that would have been difficult, if not impossible, to traverse with stiffer sheaths. This sheath has also been found to be kink resistant during a wide range of uses. These patent documents are incorporated by reference herein.

To even further increase the utility of such flexible, kink resistant sheaths, sheaths have now been developed that include one or more predetermined permanent, or semi-permanent, curves at the distal end of the sheath. Examples of such sheaths include the FLEXOR® Introducer Ansel Modification sheath and the FLEXOR® Introducer Balkin Up & Over Contralateral Design, both available from Cook Incorporated, of Bloomington, Ind. These sheaths combine the flexibility and kink resistance of a sheath, such as the sheaths described above, with a precurved distal end.

Curved sheaths are particularly useful for introducing balloons, closed and non-tapered end catheters, stents, and other medical devices into branched or otherwise hard to reach vessels. For example, the curved tip configuration allows access to the renal and contra-lateral iliac arteries from either an iliac or brachial access. This is advantageous for uses such as the delivery of a balloon and/or a stent for branch abdominal aortic aneurysm (AAA) graft placement. The curves of such sheaths may be preformed to any desired configuration, and may be selectively formed to provide access to many otherwise hard-to-reach target vessels. Such sheaths have also been sized for compatibility with either 0.018 inch or 0.038 inch wire compatible dilators.

Although distally curved sheaths have now been successfully used in numerous applications that had previously been problematic with prior non-curved sheaths, some difficulties remain. For example, for optimal results the sheath must be matched with a satisfactory dilator for use in accessing the target area. In order to provide optimal trackability, dilators have typically been formed of a composition, such as PVC, that has a stiffness at least as high as the stiffness of the sheath. The use of a stiff dilator typically causes little or no difficulty when used in combination with conventional straight sheaths. However, such dilators can be problematic when used in combination with a curved sheath, such as a sheath of the type that is used for tracking the iliac bifurcator or tortuous iliacs. In such cases, the stiff dilator has a tendency to straighten out the curve in the sheath. When this occurs, the benefits of using a curved sheath for access to the target site are essentially lost.

It is desired to provide an improved introducer assembly suitable for traversing tortuous passageways in the patient's anatomy. More particularly, it is desired to provide an introducer assembly that combines the benefits available with a curved introducer sheath with a dilator that has a stiffness such that the dilator does not appreciably straighten out the curves in the sheath during use.

BRIEF SUMMARY

The problems of the prior art are addressed by the features of the present invention. In one form thereof, the invention comprises an introducer assembly for accessing a target site in the anatomy of a patient. The introducer assembly comprises a sheath having a proximal end and a distal end, and having a lumen extending therethrough. At least a portion of the sheath distal end has a curved configuration. The assembly further includes a tapered dilator having a proximal end and a distal end. The dilator is sized to be received in the sheath lumen and has a length such that at least a distal tip portion of the dilator extends beyond the distal end of the sheath when the dilator is received in the sheath lumen. The dilator has a stiffness not exceeding a stiffness of the sheath curved portion such that the sheath substantially maintains the curved configuration when the dilator is received in the sheath lumen.

In another form thereof, the invention comprises a method for accessing a branched target site in the vasculature of a patient. A wire guide is inserted into the patient's vasculature, and threaded to the branched target site. An introducer assembly is inserted over the wire guide into the vasculature. The introducer assembly comprises a sheath having a curved distal portion, and a dilator extending through a lumen of the sheath. The dilator has a length such that at least a distal tip portion of the dilator extends beyond the curved distal portion of the sheath when the dilator is received in the sheath lumen. The dilator has a stiffness relative to a stiffness of the sheath curved portion such that the sheath substantially maintains a curvature of the curved portion when the dilator is received in the sheath lumen. The introducer assembly is passed over the wire guide such that the curved distal portion is in substantial registry with the branched target site. The curved portion of the introducer assembly is advanced over the wire guide into the branched target site.

In still another form thereof, the invention comprises an introducer assembly for accessing a target site in the anatomy of a patient. The introducer assembly comprises a sheath, a dilator, and a wire guide. The sheath has a proximal end, a distal end, and a lumen extending therethrough. The sheath includes a lubricious inner liner, a coil comprising a plurality of turns positioned longitudinally around a length of the inner liner, and an outer tube positioned longitudinally around the inner liner and connected to the inner liner through spaces between the coil turns. The outer sheath tube comprises a plurality of tube segments, wherein the segments are aligned in order of decreasing stiffness toward the distal end. At least a portion of the sheath distal end has a curved configuration, which sheath curved portion has a radius of curvature within a range of 2.0 and 2.3 inches (5.1 and 5.8 cm). At least the distal end of the sheath is provided with a hydrophilic coating. The dilator has a proximal end, a distal end, and a lumen extending therethrough. The dilator is sized to be received in the sheath lumen and has a length such that at least a distal tip portion of the dilator extends beyond the distal end of the sheath when the dilator is received in the sheath lumen. The distal tip portion is tapered to provide a generally smooth transition from the sheath distal end to an end of the distal tip portion. The dilator is formed of polyurethane, and has a stiffness less than a stiffness of the sheath curved portion such that the sheath maintains the curved configuration within the range when the dilator is received in the sheath lumen. The wire guide is sized for passage through the dilator lumen. The wire guide has a length such that at least a portion of the wire guide extends distally beyond the dilator distal portion when the assembly is positioned at the target site.

BRIEF DESCRIPTION OF THE DRAWINGS

FIG. 2 is a side view of the introducer sheath portion of the assembly of FIG. 1;

FIG. 3 is a sectional view of the distal tip portion of the sheath of FIG. 2; and FIG. 4 is a side view of the dilator portion of the assembly of FIG. 1.

DETAILED DESCRIPTION OF THE DRAWINGS AND THE PRESENTLY PREFERRED EMBODIMENTS

Figure 1:
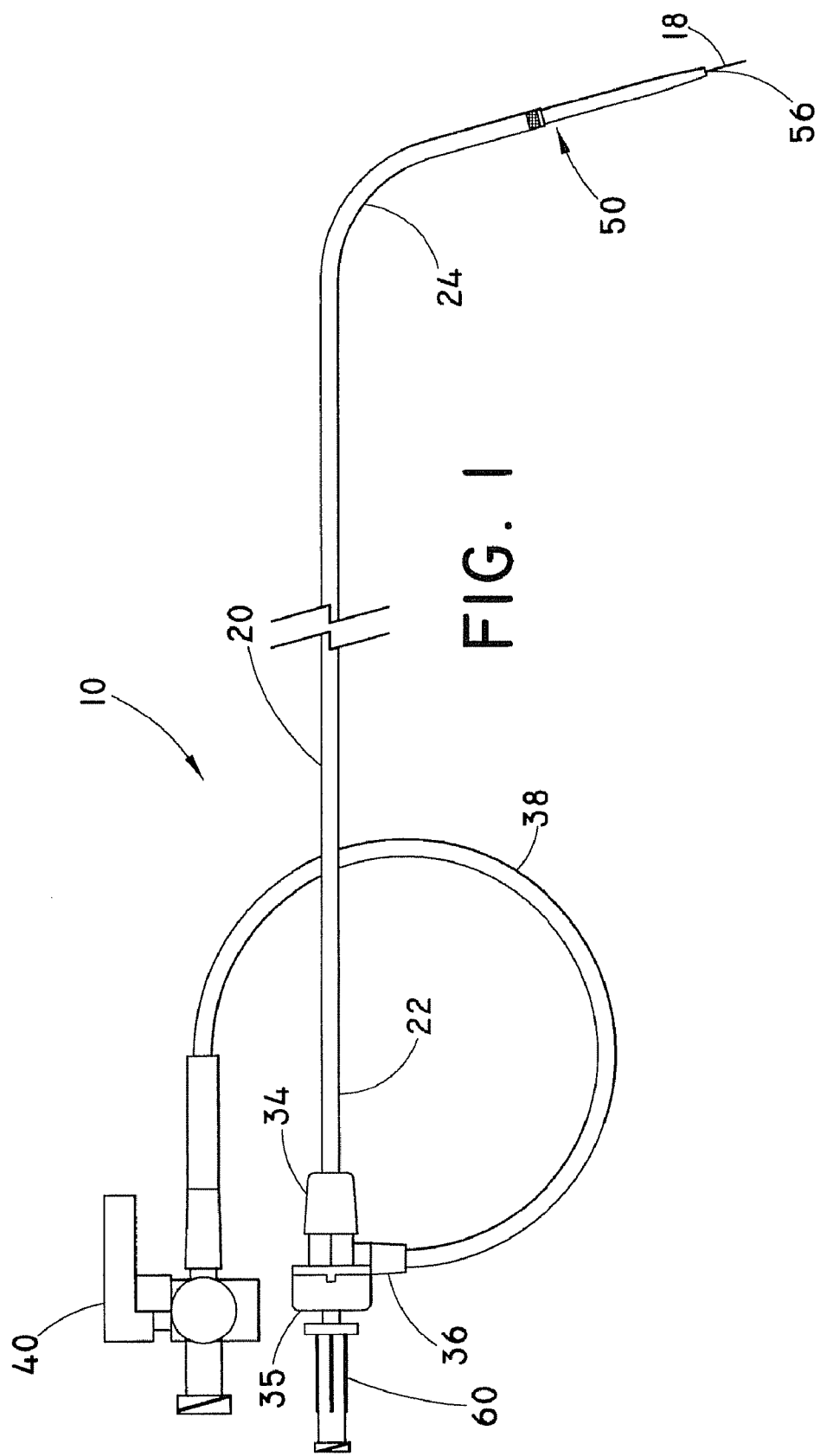
FIG. 1 is a side view of an introducer assembly according to one embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the assembly, as well as the axial ends of various components thereof. The term "proximal" is used in its conventional sense to refer to the end of the assembly (or component thereof) that is closest to the operator during use of the assembly. The term "distal" is used in its conventional sense to refer to the end of the assembly (or component thereof) that is initially inserted into the patient, or that is closest to the patient during use.

FIG. 1 illustrates a side view of an introducer assembly 10 according to an embodiment of the present invention. Among other possible uses, introducer assembly 10 may be utilized for accessing branched or otherwise hard to reach areas of the vasculature. In the embodiment shown, introducer assembly 10 includes introducer sheath 20 and dilator 50. During use, introducer assembly 10 is typically introduced over a wire guide 18 that has previously been inserted into the vasculature in conventional fashion, such as via the Seldinger percutaneous entry technique.

FIG. 2 illustrates a side view of introducer sheath 20, prior to insertion of the dilator. In this embodiment, introducer sheath 20 comprises an elongated tubular structure, having a proximal end 22 and a curved distal end 24. Introducer sheath 20 may be constructed to have any desired configuration, such as any of the configurations of the sheaths known in the art. Preferably, sheath 20 has a configuration similar to any of the sheaths described in the incorporated-by-reference U.S. Pat. No. 5,380,304 and U.S. Patent Publication No. 2001/0034514 A1. As best shown in the sectional view of the distal tip of the sheath 20 (FIG. 3), the sheath includes a passageway 25 extending longitudinally therethrough, and an inner liner 26 that extends the length of sheath 20. Preferably, inner liner 26 comprises a lubricious polymeric material, such as polytetrafluoroethylene (PTFE). A reinforcing member 28 is wound or otherwise positioned around at least a portion of the length of inner liner 26. Preferably, reinforcing member 28 comprises a flat wire coil formed of a conventional reinforcing composition. Stainless steel, metals and metal alloys (including superelastic compounds such as nitinol) are non-limiting examples of suitable compositions for the reinforcing member.

An outer layer 30 formed of a polymer, such as nylon or a polyether block amide, is adhered, bonded, or otherwise engaged with the outer surface of the inner liner by conventional means. The outer layer may comprise a plurality of tube segments, which segments are preferably aligned in order of decreasing stiffness in the direction of the distal end of the sheath. When the sheath has a plurality of segments of differing stiffness as described, in most cases a major length of the sheath (e.g., at least about 75% of the length of the sheath) that extends in the distal direction from the proximal end of the sheath will have the highest stiffness. One or more lesser lengths of the sheath extend from the high stiffness major length segment to the distal end of the sheath. Typically, the one or more segments of lesser length are aligned in order of decreasing stiffness to the distal end, thereby resulting in a sheath having a relatively gradual decrease of stiffness from the proximal end to the distal end. Those skilled in the art can readily fashion an acceptable range of stiffnesses from proximal end to distal end depending upon the proposed use of the introducer sheath assembly.

Preferably, the outer surface of the inner liner is roughened by conventional means, such as chemical etching, and the outer layer is heat shrunk onto the roughened surface of the inner liner through the coil turns. The distal tip 29 of outer layer 28 may be tapered to conform to the taper of the dilator.

If desired, a radiopaque marker band 32 may be provided adjacent the distal end of the coil. Additionally, if desired, a hydrophilic coating may be applied to the outer surface of the sheath, at least along the distal end of the sheath. Radiopaque markers and hydrophilic coatings are widely used in connection with introducer sheaths, and further description of these features is not necessary to provide an understanding of the present invention. Further description of such sheaths, and their methods of manufacture, are provided in the incorporated-by-reference patent documents.

As indicated in FIGS. 1 and 2, sheath 20 may be equipped with a hub 34. A proximal portion 35 of hub 34 may include one or more valves (not shown) therein. Typically, the valves comprise one of more conventional check-flow type disk valves, and/or a hemostatic valve. Non-limiting examples of suitable valves are disclosed in U.S. Pat. No. 7,172,580, incorporated by reference herein. Hub 34 may include a side arm 36 extending therefrom. One end of a connecting tube 38 may be engaged to side arm 36 by any conventional engagement mechanism. Connecting tube 38 is sized and positioned for transport of a fluid therethrough. A conventional control mechanism, such as stopcock 40, may be provided at the other end of connecting tube 38 for controlling flow of the fluid from a fluid source (not shown).

Introducer sheath 20 may be formed to have virtually any desired angle of curvature at the distal end. If desired, the curve may be formed at an angle that substantially conforms to the curvature of the vasculature at the intended site of entry. Forming curves to a defined angle in sheaths, such as the aforementioned FLEXOR® Introducer Ansel Modification sheath and the FLEXOR® Introducer Balkin Up & Over Contralateral Design, is now a routine operation that may readily be carried out by those skilled in the art.

Typically, the curved distal end is formed by heating the sheath in a channel of a metal forming plate or template that is shaped at a desired angle of curvature. The sheath is then allowed to cool, whereupon it substantially maintains the curvature of the channel. The curvature of the distal end of the sheath will generally be formed to fit within a predetermined tolerance. One hypothetical example of an acceptable tolerance T for the curvature of sheath distal end 24 is shown by the broken lines in FIG. 2. In this hypothetical example, any degree of curvature of distal end 24 that fits within the area designated by the broken lines would be considered acceptable for the purposes for which that hypothetical sheath is to be used.

Those skilled in the art will appreciate that the degree of tolerance acceptable for a particular sheath will vary depending upon the radius of curvature of the sheath, as well as the intended use of that sheath. In one preferred embodiment, the curve of a sheath that has a radius of curvature R that may fall within a range of 1.8 to 2.5 inches (4.6 to 6.4 cm) has a degree of tolerance is 0.7 inch (1.8 cm). More preferably, the curve of a sheath that may fall within a range of curvature R of 2.0 to 2.3 inches (5.1 to 5.8 cm) has a degree of tolerance 0.3 inch (0.8 cm).

For sheaths having larger radii of curvature, correspondingly larger degrees of tolerance will typically be acceptable. Thus, for example, if the radius of curvature of the curved portion of a sheath is about 10 inches (25.4 cm), a larger degree of tolerance of the curved distal portion will typically be acceptable when compared to a sheath having a radius of curvature of about 2.0 inches (5.1 cm). Similarly, if the radius of curvature of the curved portion is about 30 inches (76.2 cm), a larger degree of tolerance of the curved distal portion will typically be acceptable when compared to a sheath having a radius of curvature of about 10 inches (25.4 cm). Those skilled in the art can readily determine an acceptable degree of tolerance (T) for a particular radius of curvature (R), taking into account the radius of curvature of the particular sheath, as well as the intended use of the curved sheath.

FIG. 4 illustrates a side view of dilator 50. Dilator 50 comprises an elongated tubular structure, having a proximal end 52 and a distal end 54. The distal tip portion 56 of dilator 50 is tapered for accessing and dilating a vascular access site over wire guide 18 in well-known fashion. A hub 60 is provided at the proximal end of dilator 50. Dilator hub 60 is engageable with introducer sheath hub 34 in well-known fashion for selectively locking dilator 50 and sheath 20. Connection mechanisms between dilators and sheaths are very well known in the art, and further discussion of such mechanisms is not necessary for an understanding of the present invention.

Conventionally, dilators for use with introducer sheaths have been formed of a stiff material, such as polyvinyl chloride (PVC). Such stiff materials were considered necessary to achieve sufficient tracking and dilating of the access site. However, the curved (distal) portion of the sheath is often formed of a composition having less stiffness (and therefore greater flexibility) than that of the dilator. As a result, when a stiff dilator is passed through the lumen of a curved introducer sheath having a flexible distal tip, the dilator has a tendency to straighten out the curve in the distal portion of the sheath. When the curve in the sheath is straightened out, or substantially straightened out, the very purpose for which the curved sheath was employed is essentially lost, or at a minimum, is compromised.

Dilator 50 of the present invention is formed of a composition that is less stiff, and therefore more flexible, than typical dilators used in prior art assemblies having a curved introducer sheath. More particularly, dilator 50 has a stiffness that does not exceed the stiffness of the sheath curved portion, such that this sheath portion substantially maintains its curved configuration when the dilator is received in the sheath lumen. By "substantially maintains its curved configuration" is meant that the sheath curved portion maintains its same configuration prior to insertion of the dilator, or that minor variation of the curved configuration may take place. A minor variation is normally considered one that does not exceed the degree of tolerance for the curvature of the distal end of the sheath. Although it is envisioned that in most intended uses the sheath portion will maintain a curved configuration within the degree of tolerance of the curved end, those skilled in the art will appreciate that there may be some potential uses of the curved sheath wherein a variation somewhat in excess of the degree of tolerance, but less than an amount that would result in straightening out of the curved portion of the sheath, may be acceptable.

One preferred composition for use in forming dilator 50 is polyurethane. Polyurethane is more flexible than prior art dilators used for the purposes described herein, and has sufficient flexibility such that it does not straighten out the curve in conventional curved sheaths, such as the multi-layered FLEXOR® type sheaths described above. Other flexible compositions may similarly be used for forming the dilator, as long as the resulting dilator has sufficient flexibility that it does not straighten out the curve in the particular sheath used with the dilator. A non-limiting list of additional flexible compositions that may be utilized for forming dilator 50 in an appropriate case includes polyethylene, nylon and polyester.

Although specific examples of dilator compositions have been identified hereinabove, other compositions may be utilized, as long as the resulting dilator is matched with a curved sheath that has sufficient stiffness to maintain its curvature in the manner described hereinabove when the dilator is inserted therein. Thus, for example, if a particularly stiff sheath is utilized, a relatively stiff dilator may be matched with the sheath, as long as the stiffness of the dilator is insufficient to appreciably straighten out the curve in the sheath. On the other hand, when a medium or low stiffness sheath is used, the stiffness of the particular dilator utilized with that sheath may be less than the stiffness of the dilator used with the high stiffness sheath, and in any event, will be insufficient to appreciably straighten out the curve in the medium or low stiffness sheath. Thus, a wide variety of materials may be utilized to form the dilator component in the inventive assembly, as long as the dilator is matched with an appropriate sheath, as described hereinabove.

While this invention has been particularly shown and described with reference to preferred embodiments thereof, it will be understood by those skilled in the art that various changes in form and details may be made therein without departing from the spirit and scope of the invention. Those skilled in the art may recognize or be able to ascertain using no more than routine experimentation, many equivalents to the specific embodiments of the invention described specifically herein, which equivalents are intended to be encompassed in the scope of the invention.

The invention claimed is:

1. An introducer assembly for accessing a target site in the anatomy of a patient, comprising:
    a sheath having a proximal end and a distal end, and having a lumen extending therethrough, at least a portion of said sheath distal end having a curved configuration; and
    a dilator having a proximal end and a distal end, said dilator sized to be received in said sheath lumen and having a length such that at least a distal tip portion of said dilator extends beyond the distal end of said sheath when said dilator is received in said sheath lumen, said distal tip portion being tapered, said dilator having a stiffness not exceeding a stiffness of said sheath curved portion such that said sheath substantially maintains said curved configuration when said dilator is received in said sheath lumen.

2. The introducer assembly of claim 1, wherein the stiffness of the dilator is less than the stiffness of the sheath curved portion.

3. The introducer assembly of claim 1, wherein said sheath comprises an inner liner having said lumen extending therethrough; a coil comprising a plurality of turns positioned longitudinally around a length of said inner liner; and an outer tube positioned longitudinally around said inner liner and connected to said inner liner through spaces between said coil turns.

4. The introducer assembly of claim 3, wherein said outer sheath tube comprises a plurality of tube segments, said segments aligned in order of decreasing stiffness toward said distal end, and wherein said dilator has a stiffness not exceeding the stiffness of the distalmost of said tube segments.

5. The introducer assembly of claim 2, wherein said dilator comprises a flexible elastomer.

6. The introducer assembly of claim 5, wherein said flexible elastomer is selected from the group consisting of polyurethane, polyethylene, nylon and polyester.

7. The introducer assembly of claim 1, wherein said dilator comprises polyurethane.

8. The introducer assembly of claim 3, wherein said sheath inner liner comprises a lubricious polymer and said outer tube comprises at least one of a polyamide and a polyether block amide.

9. The introducer assembly of claim 8, wherein at least the distal end of the sheath is provided with a hydrophilic coating, and wherein said sheath includes a radiopaque marker at said sheath distal end.

10. The introducer assembly of claim 2, said dilator having a lumen extending therethrough, further comprising a wire guide sized for passage through said dilator lumen and having a length such that at least a portion of said wire guide extends distally beyond said dilator distal portion when said assembly is positioned at said target site.

11. The introducer assembly of claim 10, wherein said dilator taper provides a generally smooth transition from said sheath distal end to said wire guide when said wire guide is received in said dilator lumen.

12. The introducer assembly of claim 1, wherein the sheath curved portion has a radius of curvature within a range of 1.8 to 2.5 inches (4.6 to 6.4 cm).

13. The introducer assembly of claim 12, wherein said radius of curvature range is between 2.0 and 2.3 inches (5.1 and 5.8 cm).

14. The introducer assembly of claim 13, wherein said sheath maintains said radius of curvature within said range when said dilator is received in said sheath lumen.

15. A method for accessing a branched target site in the vasculature of a patient, comprising:
    inserting a wire guide into the patient's vasculature, and threading the wire guide to a vicinity of said branched target site;
    inserting an introducer assembly over the wire guide into said vasculature, said introducer assembly comprising a sheath having a curved distal portion, and a dilator extending through a lumen of said sheath, said dilator having a length such that at least a distal tip portion of said dilator extends beyond the curved distal portion of the sheath when the dilator is received in the sheath lumen, said dilator having a stiffness relative to a stiffness of said sheath curved portion such that said sheath substantially maintains a curvature of said curved portion when said dilator is received in said sheath lumen;

passing said introducer assembly over the wire guide such that said curved distal portion is in substantial registry with said branched target site; and advancing said curved portion of said introducer assembly over the wire guide into said branched target site.

16. The method of claim 15, wherein said dilator is formed of a flexible elastomer.

17. The method of claim 16, wherein said flexible elastomer is selected from the group consisting of polyurethane, polyethylene, nylon and polyester.

18. The method of claim 17, wherein said sheath comprises an inner liner having said lumen extending therethrough; a coil comprising a plurality of turns positioned longitudinally around a length of said inner liner; and an outer tube positioned longitudinally around said inner liner and connected to said inner liner through spaces between said coil turns.

19. The method of claim 15, wherein the sheath curved distal portion has a radius of curvature within a range of 1.8 to 2.5 inches (4.6 to 6.4 cm).

20. An introducer assembly for accessing a target site in the anatomy of a patient, comprising:

a sheath having a proximal end, a distal end, and a lumen extending therethrough, said sheath comprising a lubricious inner liner, a coil comprising a plurality of turns positioned longitudinally around a length of the inner liner, and an outer tube positioned longitudinally around the inner liner and connected to the inner liner through spaces between the coil turns, the outer sheath tube comprising a plurality of tube segments, said segments aligned in order of decreasing stiffness toward said distal end, at least a portion of said sheath distal end having a curved configuration formed therein, said sheath curved portion having a radius of curvature within a range of 2.0 and 2.3 inches (5.1 and 5.8 cm), at least the distal end of the sheath being provided with a hydrophilic coating;

a dilator having a proximal end, a distal end, and a lumen extending therethrough, said dilator sized to be received in said sheath lumen and having a length such that at least a distal tip portion of said dilator extends beyond the distal end of said sheath when said dilator is received in said sheath lumen, said distal tip portion being tapered to provide a generally smooth transition from said sheath distal end to an end of said distal tip portion, said dilator formed of polyurethane and having a stiffness less than a stiffness of said sheath curved portion such that said sheath maintains said curved configuration formed therein within said range when said dilator is received in said sheath lumen; and a wire guide sized for passage through said dilator lumen, said wire guide having a length such that at least a portion of said wire guide extends distally beyond said dilator distal portion when said assembly is positioned at said target site.

* * * * *